(12) United States Patent
Ollivier

(10) Patent No.: US 8,989,871 B2
(45) Date of Patent: Mar. 24, 2015

(54) PACING LEAD IN AN EXTENDED AREA OF A HEART CAVITY, IMPLANTABLE BY OVER THE WIRE TECHNIQUE IN THE DEEP CORONARY NETWORK

(71) Applicant: Sorin CRM S.A.S., Clamart Cedex (FR)

(72) Inventor: Jean-Francois Ollivier, Villiers-le-Bacle (FR)

(73) Assignee: Sorin CRM SAS, Clamart (FR)

( * ) Notice: Subject to any disclaimer, the term of this patent is extended or adjusted under 35 U.S.C. 154(b) by 116 days.

(21) Appl. No.: 13/623,400

(22) Filed: Sep. 20, 2012

(65) Prior Publication Data

US 2013/0073022 A1  Mar. 21, 2013

(30) Foreign Application Priority Data

Sep. 21, 2011  (FR) ...................... 11 58417

(51) Int. Cl.
*A61N 1/00* (2006.01)
*A61N 1/05* (2006.01)

(52) U.S. Cl.
CPC ......... *A61N 1/056* (2013.01); *A61N 2001/0585* (2013.01)
USPC ............................ 607/119; 607/122; 607/125

(58) Field of Classification Search
CPC .............................. A61N 1/056; A61N 1/0565
USPC .................................................. 607/115–119
See application file for complete search history.

(56) References Cited

U.S. PATENT DOCUMENTS

| | | |
|---|---|---|
| 5,755,735 A | 5/1998 | Richter et al. |
| 5,755,765 A | 5/1998 | Hyde et al. |
| 6,385,492 B1 | 5/2002 | Ollivier et al. |
| 7,254,450 B2 * | 8/2007 | Christopherson et al. ..... 607/119 |
| 7,483,753 B2 | 1/2009 | Ollivier et al. |
| 2008/0039916 A1 | 2/2008 | Colliou et al. |
| 2008/0177343 A1 | 7/2008 | Dal Molin et al. |
| 2009/0157136 A1 | 6/2009 | Yang et al. |
| 2011/0072659 A1 | 3/2011 | Swanson et al. |

FOREIGN PATENT DOCUMENTS

| | | |
|---|---|---|
| EP | 0993840 A1 | 4/2000 |
| EP | 1374945 A1 | 1/2004 |
| EP | 1938861 A1 | 7/2008 |

OTHER PUBLICATIONS

Foreign Search Report (Annexe Au Rapport De Recherche Preliminaire Relatif A La Damande De Brevet Francais No. FR 1158417 FA 755135), May 15, 2012.

* cited by examiner

*Primary Examiner* — Michael Kahelin
*Assistant Examiner* — Mallika D Fairchild
(74) *Attorney, Agent, or Firm* — Foley & Lardner LLP

(57) ABSTRACT

A pacing lead (20) having a lead body (22) with a central lumen and provided with structure for retaining the lead body to a wall of the coronary network, and a hollow tubular extension (26), bearing an active region of the lead and also traversed by a central lumen (28) communicating with the inner lumen of the lead body, so as to allow implantation by an over the wire technique. The hollow tubular extension has an outside diameter of between 2 and 3 French (0.66 and 1 mm) to allow implantation deep in the coronary sinus network, and it comprises on its outer surface an electrically insulated peripheral conductor, except for denuded areas intended to come into contact with the wall of a target vein and form a network of stimulation electrodes (32, 34) electrically connected together.

16 Claims, 3 Drawing Sheets

PACING LEAD IN AN EXTENDED AREA OF A HEART CAVITY, IMPLANTABLE BY OVER THE WIRE TECHNIQUE IN THE DEEP CORONARY NETWORK

RELATED APPLICATIONS

The present application claims the priority date benefit of French Patent Application No. 11/58417 entitled "Pacing Lead In An Extended Area Of A Heart Cavity, Implantable By Over The Wire Technique In The Deep Coronary Network" and filed Sep. 21, 2011.

FIELD OF THE INVENTION

The present invention relates to "active implantable medical devices" as defined by the Jun. 20, 1990 directive 90/395/CEE of the European Community Council, more specifically implanted devices that continuously monitor a patient's cardiac rhythm and deliver if and as necessary to the patie-ne5ent's heart electrical pulses for stimulation (pacing), cardiac resynchronization, cardioversion and/or defibrillation, and more specifically to cardiac pacing leads to be implanted in the coronary network of the heart to allow stimulation of a left or right heart cavity, i.e., a ventricle or atrium.

BACKGROUND

Unlike the right heart cavities for which it is sufficient to implant endocardial leads via the right peripheral venous network, the implantation of permanent leads into a left heart cavity involve substantial surgical risks, such as the risk of bubbles passing to the cerebral vasculature located downstream of the left ventricle. For this reason, when the stimulation of a left cavity is chosen, most often a stimulation lead is introduced, not into the cavity to be stimulated, but instead in the coronary network, the lead being provided with an electrode that is applied against the wall of the epicardium and oriented toward the left ventricle or the left atrium, as appropriate. These leads typically stimulate the heart muscle via one or more point electrodes whose position depends on the predefined trajectory of the cannulated vein.

A commercial lead of this type is, for example, the Situs LV model, sold by Sorin CRM (Clamart, France) and described in EP 0993840 A1 and its counterpart U.S. Pat. No. 6,385,492 (both assigned to Sorin CRM S.A.S., previously known as ELA Medical).

The U.S. Pat. Publication No. 2008/0039916 A1 and U.S. Pat. No. 5,755,735 A disclose additional examples of such leads implanted in the coronary system. The U.S. Pat. Publication No. 2011/0072659 A1, meanwhile, discloses another type of lead for deep brain stimulation.

The introduction of such a lead is via the coronary sinus, from its opening in the right atrium. The lead is then pushed and oriented along the network of the coronary veins to the selected site. This procedure is very delicate, given the peculiarities of the venous system and its access paths, including the passage of valves and tortuosities as well as the gradual reduction of the venous diameter as the lead progresses along the selected coronary vein(s).

Once the target vein is reached, the surgeon looks for a satisfactory stimulation (pacing) site, one with good electrical contact of the stimulating electrode against the tissue of the epicardium, this contact having to be maintained despite the various variations or stresses over time.

It has been proposed to have multiple electrodes along the lead body to increase the chances of an acceptable compromise, by possibly giving to the body of the lead a particular conformation. The surgeon can thus select, among the various electrodes present on the lead body, the one providing the best efficiency from both the electrical and hemodynamic points of view. Such a multi-electrode lead is described in EP 1938861 A1 and its counterpart U.S. Pat. Publication No. 2008/0177343 (both assigned to Sorin CRM S.A.S., previously known as ELA Medical) and in the U.S. Pat. Publication No. 2008/0039916 above.

These leads implement the concept of "electronic repositioning", directing or redirecting the electric field between different electrodes arranged along the pacing lead of the left ventricle and/or with one of the electrodes of the pacing lead of the right ventricle. This technology allows the management of micro-movements or changes in the hemodynamic behavior (reverse modeling), simply by reprogramming the implanted device generator via telemetry through the skin, without the burden of reoperation or further surgical intervention.

The counterpart of this solution is an increasing complexity of the structure of the lead. However, increasing the number of electrodes causes an increase in the number of components, and therefore of electrical connections, or requires the use of multiplexing circuits for the selection of the various electrodes present on the lead. All this leads to an increased risk of mechanical failure.

U.S. Pat. Publication No. 2009/157136 A1 describes a technique for finding an optimal pacing site using a temporary mapping catheter to be introduced into the coronary sinus. This catheter is either a flexible tube open at both ends, or a guidewire. In either case, it includes multiple electrically independent distal electrodes, and in the proximal portion a connector for connecting to an acquisition system for identification of the best stimulation site using an algorithm based on cardiac motion. A classic permanent definitive multielectrode lead of standard diameter from 4.5 to 6 French (1.5 to 2 mm) is then placed to the selected position, by use of a guide wire and the over the wire (OTW) technique or a tube (lumen) of the temporary catheter.

Another trend of recent developments in the field of pacing the left ventricle is the reduction of the diameter of the portion implanted in the coronary network, to a diameter of 4 French (1.33 mm). The size of the lead body is indeed a factor directly related to the controlled guiding capabilities of the lead into the coronary venous system, in order to be able to select specific stimulation sites located in certain collateral veins. These sites are reached by means of a vein sub-selection catheter used for the introduction of a guiding stylet to the chosen site. Once the vein is selected and stylet is introduced, the surgeon advances the lead body that slides over the stylet, the latter acting as a support wire of small diameter axially guiding the lead body to the selected location (OTW technique).

The above U.S. Pat. Publication No. 2008/0039916 A1 proposes to reduce the distal end portion to a diameter comprised between 1 and 5 French. Nevertheless, the multiplication of the electrodes and of the components or internal conductors necessarily implies an increase in the diameter of the lead body and reduces its flexibility, making it difficult or impossible to pass the tortuosities, which goes against the use of a small diameter and of a very high distal flexibility, features that are required in order to achieve implantation in the deepest collateral veins.

OBJECT AND SUMMARY

It is, therefore, an object of the present invention to pace a heart chamber, including the left ventricle, whose active area has a very small diameter, to exploit the full length of the vein and optimally to use or have access to use all the veins present in the basal zone.

It is another object of the present invention to provide a pacing lead that operates on an extended stimulation area, allowing (unlike traditional leads) simultaneous stimulation of several points of the epicardium. In this regard, it has been found that multiple stimulation points on the left ventricle is a factor to substantially improve the quality of cardiac resynchronization.

Yet another object of the present invention is to provide a pacing lead which has the potential to stimulate two distant areas via two distinct veins, while keeping the simplicity of implementation of a single lead. In this regard, recent studies show that it is very difficult to concurrently implant two leads in the coronary venous system. A known alternative is to equip a lead body with several electrodes, e.g., up to four electrodes in some models. However, these leads have a relatively large diameter of at least about 4 French (1.33 mm), due to the complexity of the components and of the connections necessary for the selection of the electrodes for electronic repositioning. The limitations described above on the fineness of the lead is thus present. Furthermore, the relative position of the selected pairs of electrodes is very limited, these pairs of electrodes being also necessarily positioned in the coronary vein, usually the posterolateral vein.

The present invention is thus directed to a configuration for a stimulation lead having a very small diameter, implanted in the coronary venous system, to improve the efficiency of the stimulation and offering: (i) a possibility of implantation in the patient's deep veins, (ii) a broadening of the stimulated area, and (iii) the ability to possibly stimulate simultaneously two distant areas via two distinct veins.

It is another object of the present invention is to provide a pacing lead that is simple in structure (and therefore inexpensive to manufacture, and with maximum reliability) and that overcomes the problems associated with the design and use and structural and functional complexity of multiple electrode leads.

Yet another object of the present invention is to provide a pacing lead that can be implanted by conventional techniques, well known by the practitioners, thus not requiring any additional learning or technical skills.

Broadly, the present invention is directed to a lead body of a conventional type, with an external diameter its distal end of typically between 3 and 6 French (1 and 2.66 mm), that has at its distal end a hollow tubular extension having a very small outer diameter, typically 1 to 3 French (0.33 to 1 mm), about half of the typical diameter of the current coronary leads. The inside diameter of the hollow tubular extension is, on the other hand, compatible with the passage of a guide wire of small diameter, typically a guide wire of 0.014 inches, or 1.1 French (0.356 mm).

The very small outer diameter of the hollow tubular extension allows cannulation of the very narrow veins of the coronary network, including the deep coronary network, which have not heretofore been exploited due to the larger size of the conventional permanent coronary leads.

One advantage of the present invention lies in the fact that, in the vein, the hollow tubular extension is not subject to the risk of abrasion with another device (including another lead), unlike the remaining portion of the lead body in the right atrium or the intravenous path. Consequently, the thickness of the electrically insulating exterior layer of the hollow tubular extension can be significantly reduced, thus contributing to the overall reduction in diameter of the hollow tubular extension.

Yet another aspect of the present invention is that the hollow tubular extension has on its outer surface a peripheral electrical conductor, which is isolated with the exception of a plurality of denuded areas forming a respective plurality of electrodes electrically connected together via the peripheral conductor. The denuded areas forming electrodes are advantageously preferably a plurality of denuded areas spaced apart yet divided into one or several active stimulation regions. These electrodes are designed to come into contact with the wall of a target-vein of the coronary network for the application, simultaneously in several places, of stimulation pulses on the wall of the epicardium It should be understood that it is the conductor itself that is used as an electrode (by the denuded areas which expose the underlying conductor), unlike conventional leads which typically use applied electrodes, structurally distinct from the conductor that connects them to the generator coupled to the lead.

In addition, construction and materials of the hollow tubular extension are chosen so as to give the latter the properties required to enable progression in the coronary venous system after being threaded over a guide wire (the OTW technique), namely: an axial stiffness sufficient to facilitate the transmission of forces from end to end (the so-called pushability property), distal flexibility, and a low friction coefficient of an internal central lumen for a good sliding on the guide wire (the so-called trackability).

In one embodiment, the configuration of the lead according to the present invention allows the hollow tubular extension to be introduced in a first vein (the "go" vein), then through an anastomosis to and in a second vein (the "return" vein). Distal anastomosis in the coronary venous system has indeed very frequently been found, typically 60 to 80% of the patient population. In this regard, at the end of some veins there is a passage to another vein, and thus a possibility of communication between two distinct veins at the anastomosis, via their respective distal ends.

The distribution of the electrodes (the denuded areas) of the hollow tubular extension may be chosen such that the electrodes are grouped into two separate sets, forming two separate active regions, one for the definition of the stimulation sites in the "go" vein and the other for the definition of the stimulation sites in the "return" vein. These two sets of electrodes are separated by an intermediate isolated region corresponding to the most distal parts of the "go" vein, the region of the anastomosis, and the most distal parts of the "return" vein.

In one embodiment, the present invention is directed to a pacing lead for implantation in the coronary venous system for stimulation of a heart cavity. This lead comprises, as disclosed in the above U.S. Pat. Publication No. 2008/0039916 A1, a lead body with a hollow sheath having a diameter and traversed from end to end by a central lumen, the distal end of the lead body comprising retaining means to couple the lead body distal end to a wall of the coronary network. The outside diameter of the hollow tubular extension is preferably between 1 and 3 French (0.33 and 1 mm). The distal end comprises at its outer surface at least one electrically isolated peripheral conductor to the exception of plurality of denuded areas intended to come into contact with the wall of a target vein of the coronary network, so as to constitute a network of stimulation electrodes electrically connected together. The pacing lead comprises an electrical connection of the peripheral conductor to means disposed at the proximal end of the lead body for coupling the lead to the generator of an active implantable medical device such as a pacemaker or a resynchronizer.

In one embodiment, the lead body is extended at its distal portion by a hollow tubular extension secured to the lead body and bearing an active portion of the lead, this hollow tubular extension being traversed from one end to the other by a central lumen communicating with the inner central lumen of the lead body so that it allows the introduction and sliding of a guide wire for implantation of the lead with a guide wire technique. The hollow tubular extension on its outer surface preferably comprises said electrically isolated conductor with the exception of the denuded areas.

The peripheral conductor can be a wire coiled on a hollow tube, preferably made of a biocompatible, flexible non-conductive material, said wire being electrically isolated except at the denuded areas formed on the wire. The wire is advantageously a flat wire, having a width greater than its height, which can in particular comprise a core of stainless steel sheathed by a platinum-iridium layer and covered on its surface with a layer of an insulating material. This wire can be wound in a helix about the hollow tube with non-contiguous turns, i.e., with gaps between the turns. These gaps are then filled with an insulating material that also fills the thickness of the wire between the outer surface of the hollow tube and a level flush with the level of the outer peripheral surface of the wound wire.

In one embodiment, the exposed surface area of each denuded area of the peripheral conductor is not more than 2 $mm^2$, and the total exposed surface area of these areas collectively is not more than 10 $mm^2$.

In one embodiment, the denuded areas of the peripheral conductor are grouped to form at least one active region extending over a length of between 1 and 5 cm.

In one embodiment, the lead body includes at its distal end at least one bipolar stimulating electrode, not electrically connected to the peripheral conductor of the hollow tubular extension.

In one embodiment, the denuded areas of the peripheral conductor are grouped to form at least two active regions, each extending over a length of between 1 and 5 cm and separated by an intermediate non-active region having a length of between 5 and 15 cm.

In one embodiment, the hollow tubular extension has on its outer surface two electrically distinct conductors, each being connected to respective sets of distinct denuded areas, each active region comprising at least one denuded area of each set, so as to allow bipolar pacing.

In one embodiment, the hollow tubular extension has at its distal end at least one radiopaque marker for identifying the position of the distal extension inside a patient.

In one embodiment, the retaining means at the distal end of the lead body comprises at least one relief formed on the distal end of the lead body, having locally an increased diameter relative to the outer diameter of the lead body. The relief is more preferably a helical relief with a screw thread wrapped around the lead body.

In one embodiment, the diameter of the lead body is preferably between 2 and 6 French (0.66 and 1.99 mm).

In one embodiment, the lead body has on its distal end at least one radiopaque marker for identifying the position of the proximal end of the hollow tubular extension in the patient.

Advantageously, the electrode configuration of the hollow tubular extension allows, with a single lead, simultaneous stimulation of two relatively remote regions, preferably located in two separate veins. The dual effect of distance of these two regions and of multiplication of stimulation points in each region provides a particularly beneficial effect for the resynchronization of heart function.

Advantageously, as discussed below, the lead of the present invention (formed by the lead body and its hollow tubular extension carrying the electrodes) may be implanted by conventional techniques well known to practitioners, thus not requiring any additional training or technical skill.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 generally illustrates a partial sectional view of the myocardium, with the main veins of the coronary network in which is introduced a pacing lead according to the present invention for stimulation of the left ventricle;

Figure 7:
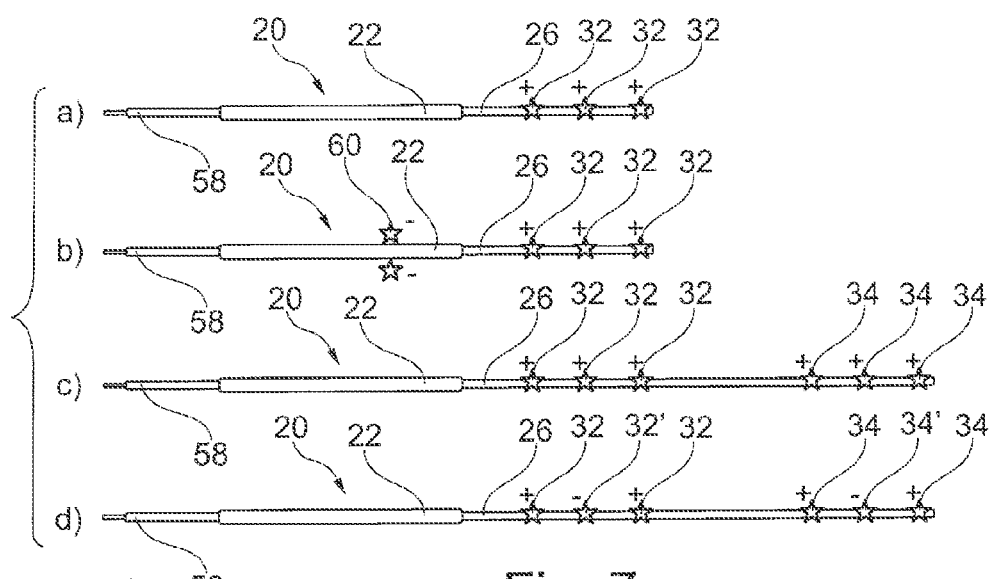

FIGS. 7a to 7d illustrate various configurations of leads of the present invention, for monopolar stimulation (FIGS. 7a and 7c) or bipolar stimulation (FIGS. 7b and 7d), and for applications of stimulation in a single vein (FIGS. 7a and 7b) or simultaneously in two different veins (FIGS. 7c and 7d).

DETAILED DESCRIPTION

With reference to the drawings FIGS. 1-7, preferred embodiments of a lead in accordance with the present invention will now be described.

Figure 1:
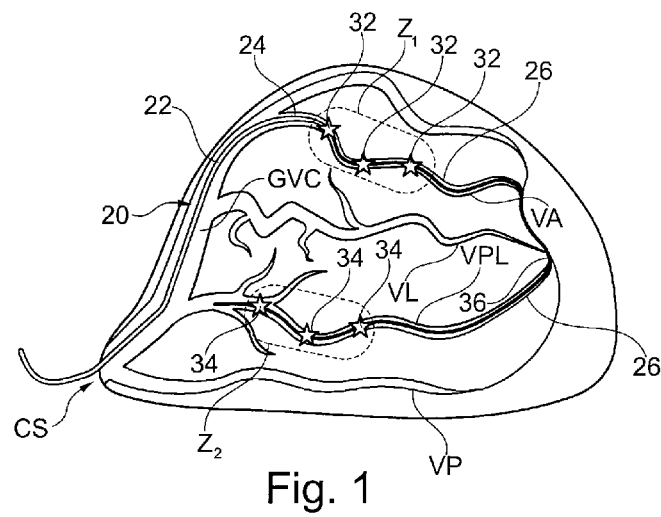

FIG. 1 generally illustrates a patient's myocardium and major vessels of the coronary network, in which a lead 20 was introduced to stimulate the left ventricle. Lead 20 is implanted in the intracardiac coronary venous system via the superior vena cava, right atrium and the input of the coronary sinus vein CS. The coronary venous system then develops into several branches from the great cardiac vein GVC, these veins branches including the posterolateral vein VPL, the lateral vein VL, the anterolateral vein VA and the posterior vein VP.

Figure 2:
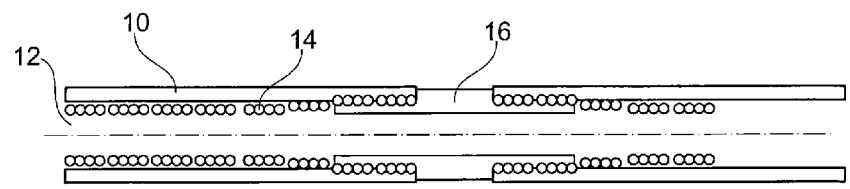
FIG. 2 illustrates a conventional structure of lead for pacing of the left ventricle according to the prior art.

FIG. 2 illustrates in cross section and schematically, in the region of the stimulation electrode, the structure of a conventional prior art pacing lead for implantation in the coronary venous system. This conventional construction comprises an electrically insulating lead body 10, with a central lumen 12 for introduction of a guide wire used for the implantation of the lead. The inner region of the lead also comprises a coiled conductor 14 (typically made of MP35N stainless steel) electrically connected to an electrode 16 (typically made of an alloy of platinum and iridium) mounted on lead body 10. Given the constraints of the dimensions of the guide wire, the insulation thickness, etc., the diameter of such a conventional lead is generally between 4 and 6 French (between 1.33 mm and 2 mm), with an internal lumen of 1.3 French (0.4 mm). Moreover, the presence of an electrode 16 introduces a discontinuity in the structure of the lead, which can have an impact on the long-term endurance (also known as durability) of the lead in case of insufficient dimensioning of the different elements.

For its implantation, the lead is inserted through the coronary sinus CS and great cardiac vein GVC, then into the anterolateral vein VA. However, given the overall outer diameter of the lead, 4.5 to 6 French (1.5 to 2 mm), it is not possible to reach the deepest veins of the coronary network. Stimulation is therefore confined to the major veins, of larger diameter, that are achievable.

Figure 3:
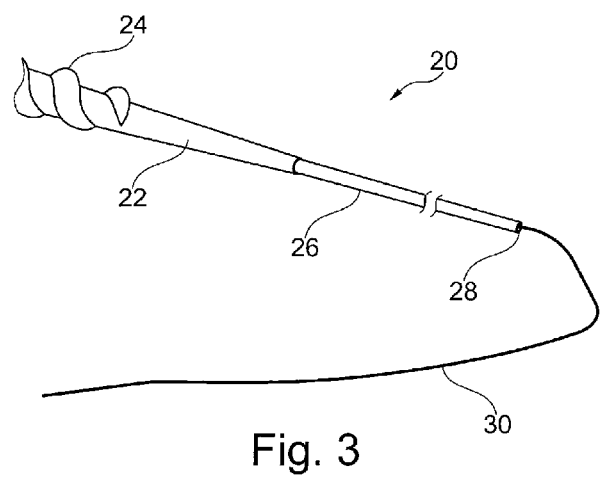
FIG. 3 is a view of an embodiment of a lead according to the present invention, showing the distal end of the lead body extended by a hollow tubular extension and the assembly being threaded onto a wire guide for implantation.

FIG. 3 illustrates the distal portion of a lead 20 according to an embodiment of the present invention, threaded over a guidewire for its implantation. Lead 20 is also represented in an implanted configuration on FIG. 1.

Lead 20 according to this embodiment of the present invention comprises a lead body 22 formed of a tubular hollow sheath made of a deformable material, for example, silicone or polyurethane, provided with a central lumen extending from one end, the proximal end, to the other, the distal end, of the body lead 22.

The outer diameter of the overall lead body 22 is between 3 and 5 French (1 and 1.66 mm), preferably not more than 4 French (1.33 mm). Lead body 22 may be optionally terminated in its most distal region by a transition portion whose diameter gradually decreases, for example, down to a value of 2 French (0.66 mm) to allow a deeper penetration in the venous system.

The outer diameter of 4 French (1.33 mm) of lead body 22 provides good abrasion resistance and contributes to the mechanical stability of the whole system by effect of mechanical support in the coronary sinus.

Lead body 22 houses an inner electrical conductor (not shown in this figure), which leads at its proximal end to a suitable connector (schematically shown at 58 in FIG. 7), for example, an IS-1 connector, factory assembled.

At its opposite end (distal), lead body 22 is provided with retaining means 24 for mechanically retaining lead body 22 in the vein. The retaining means is, for example, a silicon screw as described in EP 1374945 A1 and its counterpart U.S. Pat. No. 7,483,753 (both assigned to Sorin CRM S.A.S., previously known as ELA Medical), with a helical thread around the lead body. The helical thread is preferably integrally molded with the lead body of silicone elastomer, a minimally traumatic material providing good biocompatibility. The retaining means 24 has also schematically been shown in FIG. 1. This retaining means structure and associated function are in themselves known, e.g., of the same type as that used in the Situs LV model pacing lead previously referenced.

Typically, lead body 22 is extended at its distal portion by a hollow tubular extension 26 secured to lead body 22 and electrically connected to the active elements of lead 20. Hollow tubular extension 26 is traversed, from its proximal end to its distal end, by a central lumen 28 also communicating with the inner lumen of the lead body, so as to allow the introduction and sliding of a guide wire 30 for the implantation of lead 20 by an over the wire technique described below. Guidewire 30 is provided at its distal end with a very flexible termination so as not to be traumatic and to allow its direct introduction into the deep vessels of the coronary network without risk of perforation. Once lead 20 is in place, guide wire 30, which preferably is used only for the implantation, is removed by the surgeon.

The outside diameter of tubular extension 26 is preferably between 1 and 3 French (0.33 and 1 mm), more preferably about 2.1 French (0.7 mm), and the diameter of inner lumen 28 should be large enough to allow the introduction guide wire 30 (e.g., guide wire 30 having a typical diameter (but not limited to) of 1 French (0.33 mm).

In FIG. 1, lead 20 has been illustrated as it is in situ after implantation. Lead body 22 penetrates into coronary sinus CS and great cardiac vein GVC to the outlet of anterolateral vein VA. Hollow tubular extension 26 is deeply inserted into anterolateral vein VA, and it carries a plurality of stimulation electrodes 32 (which are described in detail later) to stimulate the left ventricle from several sites, symbolized by stars, located in vein VA in a first active stimulation region $Z_1$.

Hollow tubular extension 26 also carries, at a distance from electrodes 32, another set of electrodes 34 to stimulate the left ventricle from another vein, such as posterolateral vein VPL, via a communication by an anastomosis 36 between anterolateral vein VA and posterolateral vein VPL. Hollow tubular extension 26 passes through anastomosis 36 and the most distal regions of both veins VA and VPL along an intermediate region devoid of any electrodes, to the stimulation electrodes 34, grouped around a second active region $Z_2$, at a distance from the first active region $Z_1$.

With this configuration, it is possible not only to stimulate the left ventricle at several points along one of the veins (due to the increasing number of electrodes 32 or 34 defining one or the other of the active regions $Z_1$ and $Z_2$) but also to provide two relatively distant regions of stimulation $Z_1$ and $Z_2$, respectively, the electrode area of the electrodes 32 and that of the electrodes 34, located in proximal regions of two different veins in which it would have been difficult to fix or stabilize conventional stimulation leads of the left ventricle, because of the large diameter of the mouth of these veins.

Electrodes 32 and/or 34 are formed, as explained below, of the denuded areas of a single peripheral conductor, isolated from tubular extension 26, and together forming an array of electrodes connected together in series to multiply the points of contact with the wall of the vein. This configuration ensures a multi-zone diffusion of the stimulation energy in several points of the coronary network and thus of the left ventricle.

The individual surface of each electrode is at most 2 mm$^2$, which allows disposing a large number of electrodes not exceeding a combined total surface area of 10 mm$^2$. Due to the low cumulative surface area, the benefits of a "High current density" lead, in terms of both physiological efficacy of stimulation and of lower energy consumption—this while maximizing the likelihood of physical contact, therefore electrical, electrodes 32, 34 with excitable tissues, due to the multiplication of these electrodes, is achieved.

The quality of the physical contact between electrodes and tissue can be significantly improved by preshaping of the hollow tubular extension, for example, to have a corrugation along its length in the form of a sinusoid and preferably to place the electrodes at the top of the corrugations, for example, in the form of sinusoid periods, corresponding to the respective stimulation regions.

This conformation is preferably carried out during manufacture at the factory, each corrugation being in a preshape given to the coiled conductor (for example, by heat treatment under imposed deformation) and/or to the insulating structure in the free state, with, for example, a length of the sinusoid period of the order of 30 mm and a total amplitude in the radial direction of the order of 10 to 25 mm. Because of the elasticity of the structure, the preshapes of the corrugated portions are deformable in radial stress during passage through the veins of the coronary system, and they promote the electrode contact with the tissues, and thus the electrical performance of these electrodes (particularly if the electrodes are located at the top of the corrugations).

FIGS. 4a to 4e illustrate the successive steps of implementation of the hollow tubular extension of a lead of the invention.

The first step (FIG. 4a) is to take a wire 40 made of a conductive material and wind it according to a helical configuration. The wire 40 is advantageously a flattened section wire, which gives a better axial stiffness in tension and compression, and thus the mechanical properties favorable for pushability, that is to say the ability of tubular extension 26 of the lead to be progressively advanced over the guidewire to the coronary venous network and in the tortuosity thereof. Wire 40 may include a wire having a cross section 42 of 0.08 mm×0.16 mm and a core formed of stainless steel, for example, MP35N, coated with a layer 44 of platinum-iridium. The function of this platinum irridium coating is to create a polar surface capable of withstanding the stresses of corrosion under current flow. This wire is wound in non-touching turns, so as to leave a gap 46, e.g., on the order of 0.08 mm, between successive turns.

In the next step (FIG. 4b), the wire is subjected to a deposition of an insulating layer 48, for example, a thin layer of C type parylene having a 5 micrometers thickness.

The next step (FIG. 4c) is to insert a micro-tube 50 within this coil, for example, a PTFE micro-tube having an outside diameter of 1.4 French (0.466 mm), leaving in its center an inner lumen 28 of the order of 0.45 mm. The material provides a particularly excellent sliding of the guidewire to be introduced into the lumen 28, and also ensures the protection of the internal lumen in the next step.

This next step (FIG. 4d) is to run a backfilling operation, that is to say of filling an insulating material 52, for example, silicone, in the intervals between the remaining turns of the wire, while leaving exposed, the outer face 54 of the wire 40 covered with its insulation 48.

The final step (FIG. 4e) consists in arranging the denuded areas, i.e., openings 56 in the insulating sheath 48 so as to locally expose the conductive portion of wire 40. Preferably, ablation or laser beam plasma techniques may be used, which allows for very fine cuts (up to 0.01 mm) in the parylene insulator 48, with great flexibility in choosing the form of opening 56 and the control of its extent. It is thus possible to "program" a cutting beam path to create a "long" electrode (up to 10 mm) of a total area less than 2 mm², further increasing the likelihood of contact with the tissue without loss of electrical performance. Similarly, in the case of a bipolar lead embodiment described below, it is possible to create a long bipolar electrode but with a low inter-electrode distance (typically at least the winding pitch of the base conductor).

The locally stripped openings 56 constitute the denuded areas that form the active regions of electrodes 32 and/or 34 of stimulation lead 20 according to the invention, located on the hollow tubular extension 26.

Figure 4A:
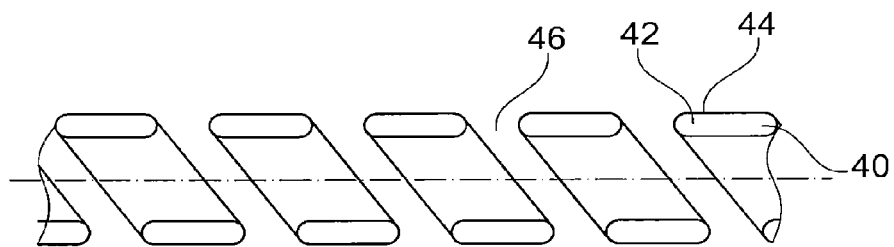
FIGS. 4a to 4e illustrate in cross section the successive steps for the realization of the hollow tubular extension of the lead of FIG. 3.
Figure 4B:
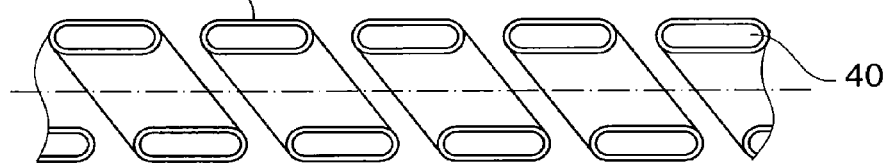
Figure 4C:
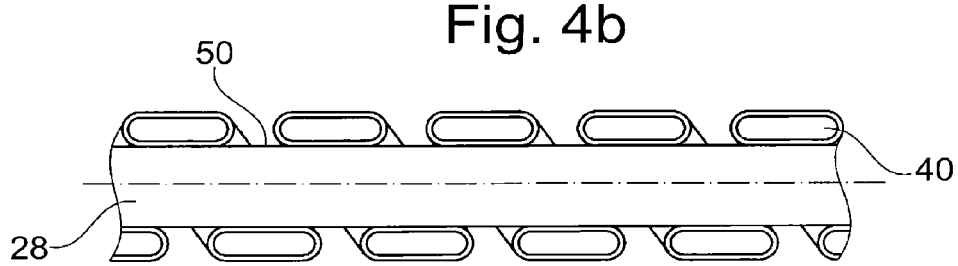
Figure 4D:
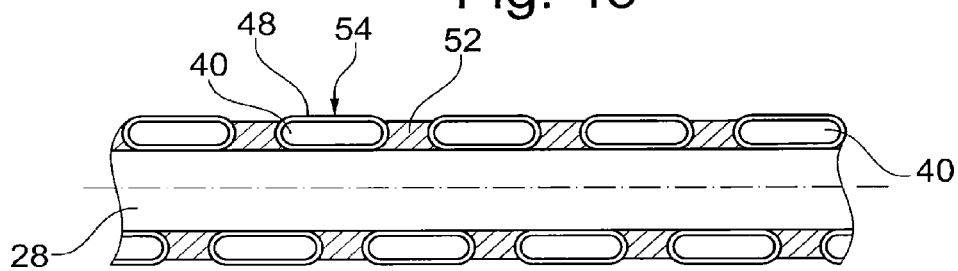
Figure 4E:
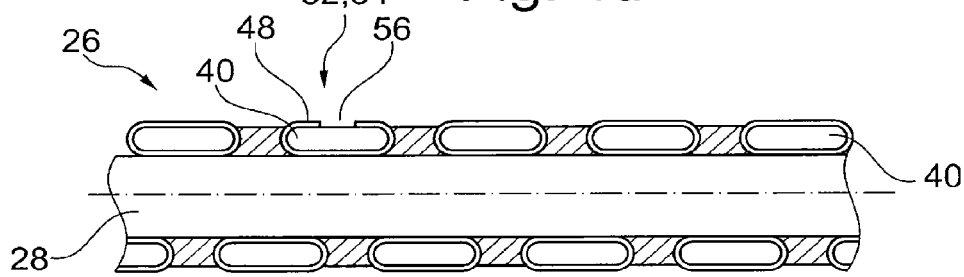
Figure 5:
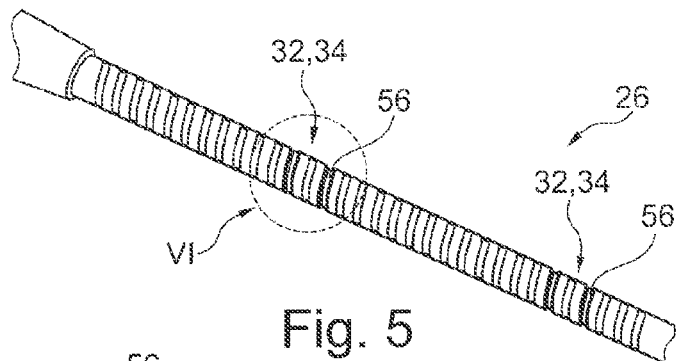
FIG. 5 is an enlarged view of a lead corresponding to FIG. 3, showing a variant on the position of the electrodes.
Figure 6:
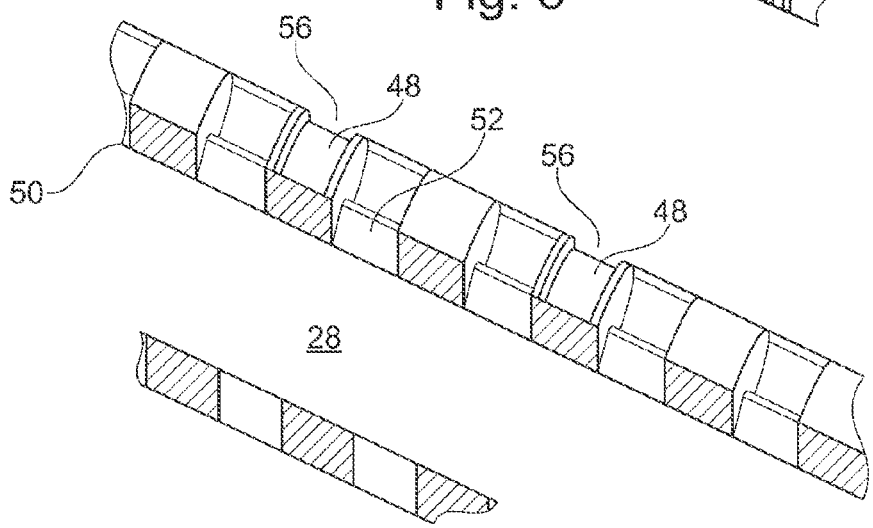
FIG. 6 is an enlarged sectional view of region VI in FIG. 5.

FIGS. 5 and 6 illustrate an alternative embodiment of applying the insulating coating 48 of parylene on the entire structure, after filling by the insulating material 52 (the step illustrated in FIG. 4d), instead of the preliminary step in FIG. 4b. Electrodes 32, 34, are formed according to the same method as above, by a selective cutting of the parylene coating revealing the locally denuded areas 56.

A further variant (not shown) is to wound not one, but several wires, for example, two or three wires, so as to give hollow tubular extension 26 either a property of redundancy that reinforces the overall reliability of the lead, or multipolarity capabilities.

Indeed, the process described above preserves the electrical isolation of the individual wires of the hollow tubular extension by two redundant insulations: parylene and silicone of the backfilling. This isolation can be preserved by connecting both wires individually to the two conductors of the lead body (this principle can be extended up to four poles).

A significant advantage of this construction is the great versatility in the realization of the configurations of the anode/cathode dipoles:

Longitudinal position of the poles along the hollow tubular extension;

Alternation of the poles within the same region $Z_1$ or $Z_2$;

Variation of the anode/cathode surfaces without creation of a rigidity point, unlike the conventional constructions.

Referring to FIGS. 7a to 7d, various embodiments of the invention are illustrated with monopolar or bipolar stimulation and/or stimulation on one or two active zones:

The embodiment of FIG. 7a corresponds a monopolar pacing in one region;

The embodiment of FIG. 7b corresponds to a bipolar pacing in one region;

The embodiment of FIG. 7c corresponds to a monopolar pacing in two distant regions (typically in two different veins);

The embodiment FIG. 7d corresponds to a bipolar pacing in two remote regions.

In the case of monopolar stimulation, corresponding to the embodiments of FIGS. 7a and 7c, the pacing pulses are respectively delivered: (i) between, on the one hand, the housing of the active implantable medical device generator and, on the other hand, electrodes 32, or (ii) between, on the one hand, the housing of the generator and, on the other hand, the electrodes 32 and 34. These electrodes are all electrically connected together and to a connector 58, for example, an IS-1 connector, located at the proximal end of the lead, for plugging in the housing.

In the case of bipolar pacing, corresponding to the embodiments of FIGS. 7b and 7d, the pulses are respectively delivered:

FIG. 7b: on the one hand, between an additional electrode 60 disposed on the lead body and, on the other hand, electrodes 32, or FIG. 7d: between positive electrodes 32 and a negative electrode 32' of a first stimulation region, and between positive electrodes 34 and a negative electrode 34' of a second stimulation region.

The connection system is a standard one: the wire(s) of the hollow tubular extension is (are) connected in the factory to the conductor(s) of the lead body, itself (themselves) connected to the terminals of the connector 58.

Finally, it should be understood that although in the various examples the active region, or each of the two active regions, is shown as comprising three electrodes (32 and/or 34), it is possible to have a smaller or larger number of electrodes in each of the active regions $Z_1$ and/or $Z_2$ wherein it is desired to stimulate.

Similarly, although we have described a stimulation of a single region ($Z_1$ or $Z_2$) of a vein, or on a single region ($Z_1$, $Z_2$) of each of two veins connected by an anastomosis, it is possible provide a greater number of stimulation regions on each vein, for example, if a stimulation in several places of one and/or the other vein is desirable.

The technique of implantation of the lead according to the invention will now be discussed.

Lead 20 is implemented by a conventional OTW technique by use of a very fine stylet forming a guide wire 30, provided at its distal end with a very flexible termination so as not to be traumatic and to allow its direct introduction in the vessels of the coronary network without risk of perforation.

Beforehand, the surgeon implants a main catheter allowing access at the mouth of coronary vein and a sub-selection catheter to choose, under fluoroscopy, the path of the venous network that will achieve the target vein.

The surgeon inserts the guide wire 30 in the sub-selection catheter, that he pushes forward into the coronary venous system in order to select a particular collateral vein, in the present case the "go" vein chosen (e.g., by the anterolateral vein VA), then—in the case of a lead to stimulate two different veins—anastomosis 26, and finally the selected "return" vein (here, posterolateral vein VPL). The surgeon then puts lead 20 with its lead body 22 and its hollow tubular extension 26 on guidewire 30, and then slides and advances it along guidewire 30 until it reaches the end. Guide wire 30 is then removed. After removal of the guidewire, lead body 22 is subjected to a screwing movement to anchor the supporting helical coil 24 at the mouth of the antero-lateral vein VA.

The configuration is then that shown in FIG. 1, with the group of electrodes 32 (and 34 if necessary) arranged in the selected stimulation region $Z_1$ (and also $Z_2$, if applicable).

As one of ordinary skill in the art will understand, these steps of vein cannulation are the same as those currently used by OTW technique specialists. Advantageously, the implantation of a lead 20 according to the present invention requires no new operating technique or specific skill.

It should be understood that the solution of the present invention allows optimal placement of the stimulation electrodes, with the guidewire 30/hollow tubular extension 26 combination of lead body 22.

It also should be understood that there is a simplicity and robustness of the assembly, despite the very small diameter. Indeed, on the hollow tubular extension, the conduction line contains no critical link such as welding or bonding providing electrical isolation, this conduction line consisting of a unique and robust element, i.e. the wire(s) of the extension.

One skilled in the art will appreciate that the present invention can be practiced by embodiments other than those described herein, which are provided for purposes of explanation, and not of limitation.

The invention claimed is:

1. A pacing lead, for implantation in the coronary venous system for stimulation of a patient's heart chamber, comprising:
   a lead body (22) comprising a hollow sheath traversed from a proximal end to a distal end by a first central lumen, the distal end of the lead body comprising means for retaining the lead to a wall of the coronary network; and
   a hollow tubular extension (26) having a proximal end and a distal end, the proximal end being secured to the distal end of the lead body, the distal end having an active lead region, said hollow tubular extension being traversed from its proximal end to its distal end by a second central lumen, the second central lumen communicating with the first central lumen of the lead body so as to allow the introduction and sliding of a guide wire through said first and second central lumens for the implantation of the lead;
   Wherein:
   the hollow tubular extension has an outside diameter of between 1 and 3 French (0.33 and 1 mm):
   the hollow tubular extension distal end comprises on its outer surface at least one electrically isolated peripheral conductor, the peripheral conductor being electrically insulated except for at least two denuded areas on an outer surface of the conductor suitable to contact a wall of a target vein of the patient's coronary network, so as to form a network of stimulation electrodes electrically connected together; and
   the lead body proximal end comprises an electrical connection for the peripheral conductor.

2. The lead of claim 1, wherein the peripheral conductor further comprises a wire wound in a helical configuration and having an outer surface, said wire being electrically insulated except for said at least two denuded areas formed on said outer surface of the wire.

3. The lead of claim 2, wherein the wound wire further comprises a flat wire having a width and a height, said width being greater than said height.

4. The lead of claim 2, wherein the wire is helically wound with non-contiguous turns, and a gap between the turns, and further comprising an insulating filling material disposed between said turns and having a thickness extending between the outer surface of the hollow tube and the outer surface of the wound wire.

5. The lead of claim 2, wherein the wire further comprises a stainless steel core, a platinum-iridium layer about the stainless steel core, and surface-coated with a layer of an insulating material.

6. The lead of claim 1, wherein the exposed surface area each denuded area of the peripheral conductor is at most 2 mm$^2$.

7. The lead of claim 1, wherein said at least two denuded areas further comprises a plurality of denuded areas and the exposed total surface of the plurality of denuded areas is not more than 10 mm$^2$.

8. The lead of claim 1, wherein the at least two denuded areas further comprise a plurality of denuded areas grouped on at least one active region extending over a length of between 1 and 5 cm.

9. The lead of claim 1, wherein the lead body distal end further comprises at least one bipolar stimulation electrode, not electrically connected to the peripheral conductor of the hollow tubular extension.

10. The lead of claim 1, wherein the at least two denuded areas further comprise a plurality of denuded areas grouped in at least two active regions separated by an intermediate non-active region, each said active region extending over a length between 1 and 5 cm and said intermediate non-active region has a length of between 5 and 15 cm.

11. The lead of claim 1, wherein the hollow tubular extension has on its outer surface two electrically distinct peripheral conductors, each being connected to respective distinct assemblies of at least two denuded areas, each active region comprising at least one denuded area for each assembly, so as to allow bipolar pacing between them.

12. The lead of claim 1, wherein the hollow tubular extension comprises at its distal end at least one radiopaque marker for identification of the position of the distal end.

13. The lead of claim 1, wherein the distal portion of the lead body further comprises a diameter, and the retention means at the distal end of the lead body comprises at least one relief formed on the lead body, locally having an increased diameter relative to the diameter of the lead body.

14. The lead of claim 13, wherein the relief further comprises a helical thread wrapped around the lead body.

15. The lead of claim 1, wherein the distal portion of the lead body further comprises a diameter of between 2 and 5 French (0.66 and 1.66 mm).

16. The lead of claim 1, wherein the lead body carries at its distal end at least one radiopaque marker for identification of the proximal position of the hollow tubular extension.

* * * * *